United States Patent [19]

Fux et al.

[11] Patent Number: 5,064,758

[45] Date of Patent: Nov. 12, 1991

[54] METHOD OF PREPARING A MIXTURE OF RIBONUCLEOTIDES

[75] Inventors: Boris B. Fux; Marina E. Shabanova; Svyatoslav N. Fedorov, all of Moscow; Jury M. Krasnopolsky, Kharkov; Uldis Y. Mixtais, Olaine; Evgeny D. Ermolaev, Olaine; Mara A. Gailuma, Olaine, all of U.S.S.R.

[73] Assignees: Institut Moreologii Cheloveka; Mezhotraslevoi Nauchno-Tekhnichesky Komplex "Mikrokhirurgiya Glaza", both of Moscow; Nauchno-Proizvodstvennoe Objedinenie "Biolar", Olaine, all of U.S.S.R.

[21] Appl. No.: 460,921

[22] PCT Filed: Dec. 20, 1988

[86] PCT No.: PCT/SU88/00269

§ 371 Date: Feb. 1, 1990

§ 102(e) Date: Feb. 1, 1990

[87] PCT Pub. No.: WO89/12689

PCT Pub. Date: Dec. 28, 1989

[30] Foreign Application Priority Data

Jun. 14, 1988 [SU] U.S.S.R. ............................. 4432648

[51] Int. Cl.$^5$ ............................................... C12P 19/30
[52] U.S. Cl. ........................................ 435/89; 435/90; 435/91
[58] Field of Search ............................. 435/89, 90, 91

[56] References Cited

U.S. PATENT DOCUMENTS

| 3,785,926 | 1/1974 | Jachertz | 514/44 |
| 3,920,519 | 11/1975 | Norimoto et al. | 435/92 |
| 4,190,649 | 2/1980 | Beljanski | 536/29 |
| 4,335,239 | 6/1982 | Beljanski | 536/29 |
| 4,758,553 | 7/1988 | Ogoshi | 514/48 |

OTHER PUBLICATIONS

Vestnik Akad. Med. Nauk. SSSR 1971, Meditsina, No. 7, pp. 63-69.

Primary Examiner—Herbert J. Lilling
Attorney, Agent, or Firm—Burgess, Ryan & Wayne

[57] ABSTRACT

A method of preparing a mixture of ribonucleotides consisting in hydrolysis of yeast nucleic acid with pancreatic ribonuclease at a pH 4.5-5.5. Thereafter, separating the ribonucleotide fraction from the obtained hydrolyzate is effective on membranes with pores sized 50-150 Å with subsequent purification and isolation of the end product.

6 Claims, No Drawings

METHOD OF PREPARING A MIXTURE OF RIBONUCLEOTIDES

BACKGROUND OF THE INVENTION

FIELD OF THE INVENTION

This invention relates to medicine and more particularly it relates to the method of preparing a mixture of ribonucleotides.

DESCRIPTION OF THE RELATED ART

Tapetoretinal abiotrophy is a group of hereditary diseases of man that are characterized by progressive loss of vision and blindness. The disease is rather common and its incidence varies from 0.2 to 5 per 1000 of population. Despite this high occurrence of taperoretinal abiotrophy, there are no effective means to treat it.

Known in the prior art is a method for preparing a mixture of ribonucleotides having medicating properties (Bulleten eksperim. biologii i meditsyny, 1989, Moscow, No. 9, p. 23-26). According to this method, ribonucleic acid with the concentration of 5-10 mg/ml is treated with pancreatic ribonuclease at a temperature of 45° C. for an hour.

The method is not very efficient. The obtained mixture of ribonucleotides contains proteins, high-molecular pyrogenic substances and can therefore only be used for external application. Oral administration of the preparation causes deep degradation of its nucleotides and the medicating effect of the preparation is thus lost.

Known in the prior art is another method for preparing a mixture of ribonucleotides (Vestnik Akad. Med. Nauk SSSR, 1971, Meditsina, No. 7, p. 63-69) by hydrolyzing ribonucleic acid with pancreatic ribonuclease and dialyzing the obtained hydrolysate with subsequent isolation and concentration of the end product. The yield of thus prepared mixture is 40-43 per cent by weight.

The method has low yield, the purity of the end product is insufficiently high due to its contamination with low- and high-molecular pyrogenic compounds. Intramuscular administration of this preparation is very painful, it evokes elevation of body temperature in most patients and allergic reactions. Subconjunctival administration causes hyperaemia and oedema of the conjunctive of the eye-ball with enlargement and tenderness of the parotid lymph nodes.

SUMMARY OF THE INVENTION

The invention is based on the problem of providing a modified method by which the yield of the end product might be increased, the quality improved, and the pyrogenic properties ruled out.

The problem is solved by providing a method for preparing a mixture of ribonucleotides by hydrolysis of ribonucleic acid with pancreatic nuclease, isolation of the ribonucleotide fraction from the hydrolyzate with subsequent isolation of the end product in which, according to the invention, ribonucleic acid is hydrolyzed at pH 4.5-5.6 with subsequent separation of the ribonucleotide fraction from the hydrolysate on membranes with pores sized 50-150 Å.

In order to increase the yield of the end product, it is recommended that hydrolysis be carried out at a temperature of 62°-65° C.

If the temperature is below 62°60 C., the enzymatic hydrolysis with pancreatic ribonuclease is slow; if the temperature is above 65° C. the enzyme is partly denatured and the resultant hydrolysis is incomplete.

In order to prevent propagation of microflora, it is recommended that before separation of the ribonucleotide fraction, ethanol be added to the hydrolysate in the quantity of 15-30 per cent by volume. If the amount of ethanol added to the hydrolysate is below 15 per cent by volume, the growth of the microflora is now slowed. If the ethanol proportion exceeds the 30 per cent limit, the ribonucleotides are partly precipitated.

The ribonucleotide fraction should preferably be separated on the membranes at a temperature of 20°-30° C. and a pressure of 0.15-0.4 MPa. Filtration of the mixture under a pressure below 0.15 MPa and a temperature below 20° C. increases substantially the time of the process without increasing the yield of the product; contamination with microflora is possible. If the pressure is above 0.4 MPa and the temperature is above 30° C., the composition of the end product can be altered and the membrane destroyed. The end product is isolated according to the invention by precipitating tue ribonucleotide fraction with 8-10 volumes of ethanol, with subsequent removal of the solvent and drying of the end product. The end product can be isolated by precipitating the ribonucleotide mixture with 8-10 volumes of ethanol, removal of the solvent, dissolving the remaining mixture in 0.55-0.66 per cent sodium chloride solution to the concentration of 3.3-3.7 per cent by weight, filtering the obtained solution through membranes with pores sized 2000-2200 Å and a pressure of 78-98 kPa. If precipitation of the ribonucleotide mixture is carried out with ethanol taken in amount below 8 volumes, the low-molecular pyrogenic impurities are not eliminated completely. If the volume of the alcohol exceeds the 10-fold volume, the positive effect of the process is not increased.

The preparation with the concentration of ribonucleotides more than 3.7 per cent by weight produces a marked pyrogenic effect, while administration of preparations with concentration below 3.3 per cent by weight requires larger volumes of liquid, which is undesirable for the patient.

If filtration is performed through membranes with the pores sized under 2000 Å, the process is slower, while filtration through pores sized over 2000 Å increases the pyrogen content and makes the preparation non-standard.

The proposed method provides an increase in the yield of the end product by 8-15 per cent compared with the known method and also improves the quality of the end product which becomes pyrogen-free.

BEST WAY OF CARRYING OUT THE INVENTION

The proposed method is carried out as follows.

Yeast nucleic acid is suspended iu distilled water. The pH of the solution is adjusted to 4.5-5.5 by adding alkali. Pancreatic ribonuclease is then added to the solution, the mixture is heated to 62°-65° C., and ribonucleic acid is hydrolyzed at this temperature. On termination of the hydrolysis, the hydrolyzate is cooled, ethanol is added, and the mixture is stirred. The fine precipitate is then separated on a microfilter. The clarified solution is fractionated by ultrafiltration through membranes with the pores sized 50-150 Å, preferably at a temperature of 20°-30° and a pressure of 0.15-0.4 MPa. After separation of the filtrate, distilled water is added to the concentrate and another portion of the filtrate is thus obtained. Ethanol is added to the collected ultra-filtrate with stirring. The mixture is allowed to stand and the supernatant is then decanted, while the precipitated product is washed with a small amount of ethanol, which is then separated on a filter, and the precipitate dried. The end product can be both solution and a dry mass. The mixture of ribonucleotides isolated after the first precipitation with 8-10 volumes of ethanol is dissolved in 0.55-0.65 per cent sodium chloride solution to attain the concentration of 3.3-3.7 per cent by weight. The obtained solution is passed through membranes with pores of 2000-2200 Å under a pressure of 78-98 kPa.

The prepared end product is a white or slightly yellowish amorphous powder, readily soluble in water and aqueous solutions of sodium chloride, sparingly soluble in ethanol and insoluble in acetone or ether. The preparation is a complex of mono-oligoribonucleotides (hectamers included , the main fraction (to 40 per cent by weight) being dinucleotides.

Thus prepared mixture of ribonucleotides has been tested clinically. The tests included the determination the field of vision, electroretinography, adaptation to darkness, and determining acuity of vision. The preparation was tested in 2500 patients. The treatment was given in 10-15 day courses. The preparation was administered intramuscularly, 150-200 mg daily, by two injections at 4-6 hour intervals.

Of the 2500 patients, 467 were treated for long periods of time and observed from 4 to 14 (and more) years.

The results of prolonged observation show that the severe progressive disease stabilized, or stabilized with improvement in 60 per cent of patients. Subjectively the patients reported improved orientation in the open air and in enclosures.

For a better understanding of the invention, the following examples of its practical embodiment are given by way of illustration.

EXAMPLE 1

70 g of yeast nucleic acid are dissolved in 430 ml of distilled water and the solution pH is adjusted to 5.1 with 2N NaOH. 140 mg of pancreatic ribonuclease are then added and hydrolysis is carried out for 5 hours at a temperature of 65° C. The overall volume of the hydrolyzate is 465 ml. The mixture is cooled to 25°-35° C. and 120 ml of ethanol are added. The recipitated substance is separated on a filter and the filtrate is passed through an acetyl cellulose membrane with pores sized 100 Å (the filtering surface of the membrane is 100 sq.cm), under a pressure of 0.4 MPa and a temperature of 30° C. The resultant filtrate has the volume of 360 ml. 70 ml portions of water are added two times to the remaining mass to obtain another 140 ml portion of the filtrate. The collected portions (500 ml) of the filtrate are mixed with 5 liters (10 volumes) of ethanol, the obtained mixture is cooled to a temperature between 0 and +4° C. and kept at this temperature for 4 hours. The precipitate is separated on a filter, washed with 0.360 l of ethyl alcohol and dried in a vacuum drier.

The yield of the end product is 36 g.

The specific extinction $E_{cm}=240$ at $\lambda$ 260 nm and pH 2. Absorption (A) at pH 7 and the wavelength of 230 nm, 260 nm and 280 nm:

| A 260/230 | 3.15 |
| --- | --- |
| A 260/280 | 1.60 |

The composition of the end product is as follows, in per cent by weight:

| nucleosides | 1.5 |
| --- | --- |
| mononucleotides | 25.6 |
| dinucleotides | 28.1 |
| trinucleotides | 23.8 |
| tetranucleotides | 12.8 |
| pentanucleotides and higher oligonucleotides - to make 100 percent. | |

EXAMPLE 2

67 g yeast nucleic acid are dissolved in 400 ml of distilled water and the pH of the solution is adjusted to 4.5 with 2N NaOH. 130 mg of pancreatic ribonuclease are added and hydrolysis is continued for 5 hours at a temperature of 62° C. The overall volume of the hydrolyzate is 430 ml. Now 64.5 ml of ethanol are added to the hydrolyzate cooled to 25°-35° C. and the mixture is filtered. Next the filtrate is passed through an acetyl cellulose membrane with pores sized 150 Å (the filtering surface 100 sq.cm) at a temperature of 20° C. and a pressure of 0.3 MPa. 380 ml of the filtrate are obtained during 6 hours. 65 ml of water are added to the remaining mass and 65 ml of filtrate are obtained in addition. The total volume of the filtrate is 445 ml. It is mixed with 3.6 liters of ethanol, the precipitated substance is separated on a filter, washed with 0.3 l of ethanol and dried in a vacuum drier.

The yield of the end product is 39 g.

The specific exinction $E_{cm}=240$ at $\lambda$ 260 nm and the pH of 2.

Absorption at pH 7 and the wavelength of 230, 260 and 280 nm are:

| A 260/230 | 3.90 |
| --- | --- |
| A 260/280 | 1.70 |

The composition of the end product in per cent by weight:

| nucleosides | 4.8 |
| --- | --- |
| mononucleotides | 19.3 |
| dinucleotides | 23.1 |
| trinucleotides | 20.2 |
| tetranucleotides | 16.9 |
| pentanucleotides and higher oligonucleotides to make 100 percent | |

EXAMPLE 3

77 g of yeast nucleic acid are dissolved in 460 ml of distilled water and the pH of the solution is adjusted to 5.2 with 2N NaOH. 150 mg of pancreatic ribonuclease are added and hydrolysis is continued for 5 hours at a temperature of 65° C. The total volume of the hydrolyzate is 500 ml. The hydrolyzate is cooled to 25°-35° C. and 150 ml of ethanol are added. The precipitated substance is separated on a filter, the filtrate is passed through an acetyl cellulose membranes with pores sized 50 Å (the filtering surface, 100 sq.cm) under a pressure of 0.2 MPa and a temperature of 25° C. for 4 hours. The filtrate (560 ml) is mixed with 8 volumes (4.5 liters) of ethanol and the obtained mixture is cooled to a temperature between 0 and +4° C. and kept at this temperature for 4 hours. The precipitate is separated on a filter, washed with 0.4 liter of ethanol and dried in a vacuum drier.

The yield of the end product is 40 g.

The specific extinction $E_{cm}=223$ at $\lambda$ 260 nm and pH 2. The optic absorption ratio at pH 7 and a wavelength of 230, 260 and 280 nm is

| A 260/230 | 4 |
|---|---|
| A 260/280 | 1.55. |

The composition of the end product in per cent by weight:

| nucleosides | 2.1 |
|---|---|
| mononucleotides | 12.6 |
| dinucleotides | 25.2 |
| trinucleotides | 24.2 |
| tetranucleotides | 18.5 |
| pentanucleotides and higher oligonucleotides to make 100 percent | |

EXAMPLE 4

Yeast nucleic acid is hydrolyzed and the ribonucleotide fraction separated as described in Example 1. The precipitate (36 g of dry mixture) is dissolved in a 0.6 per cent sodium chloride solution (958 ml) in distilled water and the mixture is stirred to complete dissolution. The obtained yellow solution is passed through a cotton wool and gauze filter and then through a membrane with pores sized 2000 Å under a pressure of 98 kPa. The ribonucleotide solution is placed in sterile conditions in ampoules of neutral glass (3 ml) and treated in an autoclave at a temperature of 119° C. for 34 minutes. The concentration of ribonucleotides in the end product is 3.3 per cent; the specific gravity is 1.01. Thus prepared product is non-toxic, sterile, and pyrogen-free. Its composition is the same as specified in Example 1.

EXAMPLE 5

The hydrolysis and of yeast nucleic acid and separation of the ribonucleotide fraction are performed as described in Example 2. The precipitate (39 g of dry mass) is dissolved in a 0.55 per cent sodium chloride solution (995 ml) in distilled water and mixed to complete dissolution. The obtained yellow solution is passed through cotton and gauze filter and then through a membrane with pores sized 2200 Å under a pressure of 78 kPa. The solution of ribonucleotides is placed in 3 ml ampoules of neutral glass in sterile conditions and treated in an autoclave at a temperature of 122° C. for 32 minutes. The concentration of ribonucleotides in the end product is 3.7 per cent, the specific gravity 1.008. The end product is non-toxic, sterile and pyrogen-free. Its composition is the same as specified in Example 2.

INDUSTRIAL APPLICABILITY

The mixture of ribonucleotides prepared by this method can be used in the medical practice as a drug for treating tapetoretinal abiotrophics. The mixture can also be used for treating myopathy, a number of immune deficiency, injuries, burns and diseases.

The method is also suitable for preparing other biologically active compounds—individual oligonucleotides and their mixtures, low-molecular proteins, peptides.

We claim:

1. A method for preparing a ribonucleotide mixture comprising hydrolysis of yeast ribonucleic acid with pancreatic ribonuclease, separation of the ribonucleotide fraction from the obtained hydrolyzate with subsequent isolation of the end product, wherein the hydrolysis of the yeast ribonucleic is carried out at pH 4.5 to 5.5 and the separation of the ribonucleotide fraction from hydrolysate is effected on membranes with pores sized 50 to 150 Å.

2. A method according to claim 1, wherein the hydrolysis is carried out at 62°-65° C.

3. A method according to claims 1-2, wherein before separation of the ribonucleotide fraction, ethanol is added to the hydrolyzate in the amount of 15-30 per cent of the hydrolyzate volume.

4. A method according to claim 1, wherein the ribonucleotide fraction is separated on membranes at a temperature of 20°-30° C. and a pressure of 0.15-0.4 MPa.

5. A method according to claim 1, wherein the end product is isolated by precipitating the ribonucleotide fraction with 8-10 volumes of ethanol with subsequent removal of the solvent and drying of the end product.

6. A method according to claim 1, wherein the end product of the method is isolated by precipitating the ribonucleotide fraction with 8-10 volumes of ethanol with subsequent removal of the solvent, dissolution of the mixture in 0.55-0.65 per cent sodium chloride solution to the concentration of 3.3-3.7 per cent by weight, and filtration of the obtained solution through membranes with pores sized 2000-2200 Å under a pressure of 78-98 kPa.

* * * * *